US010307400B2

(12) United States Patent
Gujjar et al.

(10) Patent No.: US 10,307,400 B2
(45) Date of Patent: Jun. 4, 2019

(54) ORALLY DISINTEGRATING TABLET CONTAINING ASENAPINE

(71) Applicant: ALFRED E. TIEFENBACHER (GMBH & CO. KG), Hamburg (DE)

(72) Inventors: Chaitanya Yogananda Gujjar, Shimoga (IN); Bala Ramesha Chary Rallabandi, Hyderabad (IN); Pradip Shivraj Patwari, Latur (IN); Ansgar Fitzner, Hamburg (DE)

(73) Assignee: ALFRED E. TIEFENBACHER (GMBH & CO. KG), Hamburg (DE)

( * ) Notice: Subject to any disclaimer, the term of this patent is extended or adjusted under 35 U.S.C. 154(b) by 0 days.

(21) Appl. No.: 15/426,462

(22) Filed: Feb. 7, 2017

(65) Prior Publication Data
US 2017/0143670 A1    May 25, 2017

Related U.S. Application Data

(63) Continuation of application No. 14/651,029, filed as application No. PCT/EP2013/003692 on Dec. 6, 2013, now Pat. No. 9,597,291.

(60) Provisional application No. 61/755,716, filed on Jan. 23, 2013, provisional application No. 61/755,708, filed on Jan. 23, 2013.

(30) Foreign Application Priority Data

Dec. 11, 2012  (IN) ............................ 3802/DEL/2012
Dec. 11, 2012  (IN) ............................ 3803/DEL/2012
Dec. 11, 2012  (IN) ............................ 3804/DEL/2012

(51) Int. Cl.
*A61K 31/407*    (2006.01)
*A61K 9/20*      (2006.01)
*A61K 9/00*      (2006.01)

(52) U.S. Cl.
CPC .......... *A61K 31/407* (2013.01); *A61K 9/0053* (2013.01); *A61K 9/0056* (2013.01); *A61K 9/2013* (2013.01); *A61K 9/2054* (2013.01); *A61K 9/2059* (2013.01); *A61K 9/2077* (2013.01); *A61K 9/2095* (2013.01)

(58) Field of Classification Search
CPC .. A61K 9/0056; A61K 9/2013; A61K 9/2059; A61K 31/407
See application file for complete search history.

(56) References Cited

U.S. PATENT DOCUMENTS

| | | | |
|---|---|---|---|
| 7,727,553 B2 | 6/2010 | Fujihara | |
| 2004/0265375 A1* | 12/2004 | Platteeuw | ............ A61K 9/0056 424/464 |
| 2008/0039621 A1 | 2/2008 | Maruyama | |
| 2008/0090892 A1 | 4/2008 | Casteel | |
| 2011/0053942 A1* | 3/2011 | Fujiwara | .............. A61K 9/0056 514/239.5 |

FOREIGN PATENT DOCUMENTS

| | | |
|---|---|---|
| EP | 1 710 245 A1 | 10/2006 |
| WO | WO 95/23600 A1 | 9/1995 |
| WO | WO 2008/040816 A1 | 4/2008 |
| WO | WO-2008040816 * | 4/2008 |
| WO | WO 2010/125084 A1 | 11/2010 |
| WO | WO 2010/125087 A1 | 11/2010 |
| WO | WO 2011/159903 A2 | 12/2011 |

OTHER PUBLICATIONS

Catalent Pharma Solutions, "Zydis® Fast-Dissolve Technology," Product Brochure, 2009, pp. 1-7.
International Search Report, issued in PCT/EP2013/003692, dated Mar. 20, 2014.

* cited by examiner

*Primary Examiner* — Jianfeng Song
(74) *Attorney, Agent, or Firm* — Birch, Stewart, Kolasch & Birch, LLP

(57) ABSTRACT

The present invention relates to an orally disintegrating tablet (ODT) containing asenapine maleate and to a process for preparing the ODT. In a first aspect, the present invention relates to an ODT containing asenapine maleate and low substituted hydroxypropylcellulose. In a second aspect, the present invention relates to an ODT containing crystalline asenapine maleate and the ODT is prepared using conventional tabletting techniques as direct compression and granulation. In a third aspect, the present invention relates to an ODT containing asenapine maleate and a carboxylic acid, and to the use of a carboxylic acid for enhancing storage stability of an asenapine maleate containing ODT.

16 Claims, No Drawings

ORALLY DISINTEGRATING TABLET CONTAINING ASENAPINE

CROSS REFERENCE TO RELATED APPLICATIONS

This application is a continuation of U.S. application Ser. No. 14/651,029 filed Jun. 20, 2015, which is the National Phase of PCT/EP2013/003692 filed on Dec. 6, 2013, which claims priority under 35 U.S.C. 119(e) to U.S. Provisional Application No. 61/755,708 filed on Jan. 23, 2013 and U.S. Provisional Application No. 61/755,716 filed on Jan. 23, 2013 and under 35 U.S.C. 119(a) to Patent Application No. 3803/DEL/2012 filed in India on Dec. 11, 2012, Patent Application No. 3802/DEL/2012 filed in India on Dec. 11, 2012 and Patent Application No. 3804/DEL/2012 filed in India on Dec. 11, 2012, all of which are hereby expressly incorporated by reference into the present application.

In a first aspect, the present invention relates to an orally disintegrating tablet containing asenapine maleate and low substituted hydroxypropylcellulose.

In a second aspect, the present invention relates to an orally disintegrating tablet containing asenapine maleate in crystalline form. The orally disintegrating tablet of the present invention is obtained by compressing a mixture containing crystalline asenapine maleate and pharmaceutical excipients.

In a third aspect, the present invention relates to an orally disintegrating tablet containing asenapine maleate and a carboxylic acid.

Asenapine or trans-5-chloro-2-methyl-2,3,3a,12b-tetrahydro-1H-dibenz[2,3:6,7]-oxepino[4,5-c]pyrrolidine is an atypical antipsychotic that exhibits high affinity for serotonin, dopamine, α-adrenergic and histamine receptors. Asenapine acts as an antagonist at these receptors. The drug is approved for the treatment of schizophrenia, and for the acute treatment of manic or mixed episodes associated with bipolar I disorder in a monotherapy or in a combination therapy together with lithium or valproate. Asenapine is marketed under the trade names Saphris® or Sycrest® in the form of sublingual tablets containing 5 mg or 10 mg asenapine (as maleate salt).

WO 95/23600 reports that the oral administration of conventional asenapine tablets leads to severe cardiotoxic side effects as postural hypotension and impaired baroreceptor functioning. The sublingual or buccal administration of asenapine produces substantially less cardiovascular side effects. WO 95/23600 describes a sublingual or buccal tablet containing asenapine maleate, partially hydrolyzed gelatin and mannitol. The sublingual tablet is prepared by dissolving asenapine maleate, partially hydrolyzed gelatin and mannitol in water, placing the obtained mixture into cylindrical depressions of a polyvinylchloride sheet, freezing the mixture within the depressions, subjecting the frozen mixture to freeze-drying and finally sealing the sheet with an aluminium foil to obtain a blister containing the freeze-dried sublingual tablets. The lyophilization process described in WO 95/23600 is based on the Zydis® technology (Catalent). To create an orally disintegrating tablet using the Zydis® technology, the drug is disposed in a matrix consisting of a polymeric structure former, e.g. partially hydrolyzed gelatin, and a saccharide, typically mannitol, dissolved in water. This mixture is dispensed into pre-formed blister packs, and after freezing, the product is lyophilized. The dried blisters are finally sealed. The tablets prepared using the Zydis® technology have a high porosity, which leads to a rapid penetration of water when placed in the oral cavity and, thus, to a quick disintegration of the tablet. A disadvantage of Zydis® tablets are their low hardness, so that they tend to break easily.

WO 2010/125084 and WO 2010/125087 describe a modified lyophilization process based on the Zydis® technology, in which the lyophilisate is not prepared in the final tablet package. Instead, a frozen pellet or tablet is prepared by placing the aqueous initial mixture in a cavity tray made from, e.g. steel, and extracting heat from the liquid formulation by conduction through the cavity wall in order to freeze the formulation. The frozen product is removed from the cavity tray and subjected to lyophilization. It is reported that an orally disintegrating tablet (ODT) with improved mechanical strength can be obtained by the modified lyophilization process.

Apart from using a lyophilization process, orally disintegrating tablets may also be prepared by conventional tabletting techniques as subjecting a powder mixture containing a drug and a disintegrant to direct compression. WO 2008/040816 discloses a process for preparing a sublingual tablet containing asenapine by subjecting a mixture containing amorphous asenapine maleate, starch, acesulfame potassium as sweetener, croscarmellose sodium as disintegrant, and magnesium stearate as lubricant to compression. The amorphous asenapine maleate is prepared by freeze-drying an aqueous solution of this drug.

According to EP-A-1 710 245 two crystalline forms of asenapine maleate exist: a monoclinic form, designated as form H, having a melting point of from 141° C. to 145° C., and a orthorhombic form, designated as form L, having a melting point in the range of 138° C. to 142° C. These two forms are further characterized by their respective XRD-pattern and Raman spectrum. It is further reported in EP-A-1 710 245 that micronization of the asenapine maleate is required in order to enhance its dissolution rate, when incorporated into a sublingual tablet. It was found that the monoclinic form H partly converts into the orthorhombic form L during micronization, so that a uniform polymorphic composition cannot be achieved for a micronized form H. According to EP-A-1 710 245, the orthorhombic form L is stable and does not convert into other crystalline forms, when subjected to micronization. Hence, it is advisable to use the orthorhombic form L of asenapine maleate for the preparation of a sublingual tablet, if micronization of the drug is required.

On the other hand, WO 2011/159903 discloses a process for the preparation of a crystalline asenapine maleate, which is the monoclinic form H as defined in EP-A-1 712 245, that can be subjected to micronization without deterioration of the polymorphic purity.

Hence, several techniques are employed in the state of the art for preparing asenapine maleate containing orally disintegrating tablets, e.g. sublingual tablets. These techniques are based on the Zydis® technology, direct compression of an amorphous asenapine maleate prepared by freeze-drying, and the use of a micronized crystalline form of asenapine maleate, which is the orthorhombic form L due to its polymorphic stability during micronization.

It was the object of the present invention to provide an orally disintegrating tablet containing asenapine maleate, which dissolution profile is essentially independent of the drugs' solid state. Furthermore it was the object of the present invention to provide an orally disintegrating tablet containing asenapine maleate as an alternative to the tablet prepared using the Zydis® technology.

This object is solved by the subject matter as defined in the claims.

In a first aspect of the invention, it has been found that a sufficiently high dissolution rate can be achieved, if asenapine maleate is contained in a solid matrix together with low substituted hydroxypropylcellulose (L-HPC), i.e. if the drug is contained in an L-HPC matrix. The orally disintegrating tablet (ODT) according to the present invention contains asenapine maleate, L-HPC, and a pharmaceutical excipient.

In a second aspect of the invention, it has been found that a sufficiently high disintegration time can be achieved, even if the asenapine maleate is contained in the orally disintegrating tablet (ODT) in a crystalline form. Surprisingly, a sufficiently high disintegration rate can be achieved, if the tablet is prepared using conventional tabletting techniques, i.e. by compression of a mixture containing the drug and pharmaceutical excipients. The ODT of the present invention is a compressed tablet, while the Zydis® technology does not include a compression step. The ODT of the present invention can be prepared by direct compression, i.e. by subjecting a powder mixture containing crystalline asenapine maleate and pharmaceutical excipients to compression, or by granulation, including dry granulation and wet granulation, wherein the dry granulation is preferred for preparing the ODT.

In a third aspect of the invention, it has been found that storage stability of an asenapine maleate containing orally disintegrating tablet (ODT) can be enhanced, if the ODT contains a carboxylic acid as a pharmaceutical excipient. The term "carboxylic acid" means a branched or unbranched, saturated or unsaturated carboxylic acid containing 2 to 10 carbon atoms optionally substituted with one or more hydroxy (—OH), amino (—NH$_2$) and/or mercapto (—SH) groups. The carboxylic acid used in the present invention may be selected from monocarboxylic acid, dicarboxylic acid, tricarboxylic acid, and mixtures thereof. Preferably, the ODT according to the present invention contains a $C_{2-6}$ carboxylic acid optionally substituted with at least one of hydroxy, amino and mercapto. Examples of suitable carboxylic acids include glycolic acid, oxalic acid, malonic acid, succinic acid, maleic acid, fumaric acid, tartaric acid, malic acid, glutaric acid, citric acid and gluconic acid. Examples of carboxylic acids with amino substituents include the class of amino acids, e.g. aspartic acid, glutamic acid, serine, threonine, cysteine, glycine, alanine, valine, isoleucine and leucine, and the enantiomers thereof. According to a preferred embodiment of the present invention the ODT contains a $C_4$ dicarboxylic acid optionally substituted with hydroxy; preferably succinic acid, maleic acid, fumaric acid or tartaric acid. Most preferred is tartaric acid.

Usually, the ODT contains the carboxylic acid in an amount of 0.2 to 2.0% by weight, preferably 0.5 to 1.5% by weight and more preferred 0.75 to 1.25% by weight, based on the total weight of the tablet.

With regard to the third aspect of the invention, it has been found that a sufficiently high dissolution rate can be achieved, if asenapine maleate is contained in a solid matrix together with low substituted hydroxypropylcellulose (L-HPC), i.e. if the drug is contained in an L-HPC matrix. Hence, the ODT according to the present invention preferably contains asenapine maleate, a carboxylic acid and L-HPC.

With regard to the first, the second, and also the third aspect of the invention, it was found that low substituted hydroxypropylcellulose promotes both the disintegration of the tablet and the dissolution rate of the asenapine maleate. L-HPC has a hydroxypropoxy content of 5% to 16% (USP 35-NF 30). Suitable L-HPCs having a hydroxypropoxy content of 8% or 11% are marketed by Shin-Etsu. Preferably, the L-HPC used in the present invention has a hydroxypropoxy content of 11% and is micronized (corresponding to the LH-31 grade) or non-micronized (corresponding to the LH-21 grade).

An ODT is a drug dosage form designed to be dissolved within the oral cavity. Orally disintegrating tablets include sublingual tablets and buccal tablets, the former are placed under the tongue and the latter are placed in the buccal pouch, and allowed to be dissolved in saliva. The term "orally disintegrating tablet" refers to a tablet which disintegrates within 3 min in water (37±2° C.), as determined according to the disintegration test disclosed in the European Pharmacopoeia 7.1, 2.9.1, preferably within 1 min, and more preferred within 30 seconds.

In all three aspects, according to a preferred embodiment of the present invention, the asenapine maleate is contained in the ODT in micronized form. Milling or micronization techniques that may be used for particle size reduction include sifting, milling by, e.g. ball, roller, and hammer mills, as well as jet mills. The particle size distribution of asenapine maleate particles may be measured using any technique known in the art, e.g. by microscopy or light scattering equipment such as a Malvern Mastersizer 2000. The particle size distributions can be expressed in terms of D(90), D(50) and D(10) values, where the values (expressed in μm) are the maximum sizes for 90, 50 and 10% of the particles, respectively. A micronized asenapine maleate, which can be employed in the present invention, has a particle size distribution, according to which D(90) is equal or less than 90 μm, preferably ≤30 μm, more preferred ≤20 μm and most preferred ≤15 μm. The D(50) value is equal or less than 20 μm, preferably ≤15 μm, more preferred ≤10 μm and most preferred ≤6 μm. The D(10) value is equal or less than 10 μm, preferably ≤5 μm, more preferred ≤3 μm and most preferred ≤1.5 μm. Hence, most preferred is the use of a micronized asenapine maleate having a particle size contribution of D(90) ≤15 μm, D(50) ≤6 μm and D(10) ≤1.5 μm.

The orally disintegrating tablet according to the first, the second, and the third aspect of the present invention may be prepared using a direct compression method or a granulation technique (wet or dry granulation), wherein dry granulation is preferred. If dry granulation is employed for preparing the ODT, the asenapine maleate and L-HPC is preferably contained therein as intragranular components. According to an even more preferred embodiment of the present invention, the asenapine maleate and L-HPC are the sole intragranular components, i.e. no other excipients are employed in the dry granulation procedure. If wet granulation is employed for preparing the ODT, the asenapine maleate and L-HPC is preferably contained therein as intragranular components. A mixture of asenapine maleate and L-HPC, and optionally further excipients, is wet granulated with water, an alcohol such as ethanol or isopropyl alcohol, or mixtures thereof as granulation liquid. The granulation liquid may optionally contain a binder such as povidone, copovidone, hydroxypropylmethyl cellulose or hydroxypropyl cellulose. Preferably the granulation liquid is isopropyl alcohol and the binder is povidone.

Usually, the weight ratio of asenapine maleate to L-HPC in the ODT of the present invention is from 0.5 to 1.5, preferably 0.7 to 1.2, and more preferred 0.9 to 1.1. However, if wet granulation is employed for preparing the ODT, the weight ratio of asenapine maleate to L-HPC in the ODT of the present invention is preferably from 0.5 to 3.5, more preferred 1.5 to 3.5, and most preferred 2.5 to 3.0.

In the third aspect of the invention, it is preferred that the carboxylic acid is contained in the tablet as extragranular component.

In the first and third aspect of the invention the asenapine maleate may be contained in the ODT of the present invention in amorphous or crystalline form. With regard to the second aspect, the ODT according to the present invention may contain the monoclinic form H of asenapine maleate or the orthorhombic form L as defined in EP-A-1 710 245 or a mixture of the forms H and L. In all three aspects of the invention, preferably, the monoclinic form H of the drug is contained. It has been found that the saturation solubilities of the crystalline forms L and H are different. The saturation solubility of the form H in various dissolution media is generally higher than that found for the form L. Higher saturation solubilities promote the dissolution rate, so that according to a preferred embodiment of the present invention the asenapine maleate is contained in the ODT in the crystalline form H.

In the first aspect of the invention, the ODT of the present invention is prepared using conventional tabletting techniques as direct compression and dry granulation. No lyophilization of a premix within blisters (Zydis® technology) is required. The ODT of the present invention may be prepared using a direct compression technique, comprising the method steps of:
i) preparing a mixture consisting of asenapine maleate, L-HPC and pharmaceutical excipients, and
ii) subjecting the mixture obtained in step (i) to compression to obtain the tablet.

Alternatively, the ODT may be prepared by dry granulation comprising the method steps of:
i) preparing a mixture containing asenapine maleate and L-HPC,
ii) compacting the mixture obtained in step (i) to form a comprimate,
iii) converting the comprimate obtained in step (ii) into a granulate,
iv) optionally mixing the granulate obtained in step (iii) with a pharmaceutical excipient, and
v) subjecting the granulate obtained in step (iii) or the mixture obtained in step (iv) to compression to obtain the tablet.

According to a preferred embodiment of the dry granulation procedure, the mixture in step (i) consists of asenapine maleate and L-HPC, and the granulate obtained in step (iii) is mixed with a pharmaceutical excipient.

Preferably, method step (ii) is carried out using roller compaction or slugging techniques, while method step (iii) is carried out by screening or milling the comprimate.

Alternatively, the ODT may be prepared by wet granulation comprising the method steps of:
i) preparing a mixture containing asenapine maleate and L-HPC,
ii) granulating the mixture obtained in step (i) with a granulation liquid to form a wet granulate,
iii) drying the wet granulate obtained in step (ii) to form a dry granulate,
iv) optionally mixing the granulate obtained in step (iii) with a pharmaceutical excipient, and
v) subjecting the granulate obtained in step (iii) or the mixture obtained in step (iv) to compression to obtain the tablet.

According to a preferred embodiment of the wet granulation procedure, the granulate obtained in step (iii) is mixed with a pharmaceutical excipient and a carboxylic acid. According to an even more preferred embodiment of the wet granulation procedure, the granulation liquid in step (ii) consists of isopropyl alcohol and it contains povidone.

In the second aspect of the invention, the ODT of the present invention is prepared using conventional tabletting techniques as direct compression and dry granulation. No lyophilization of a premix within blisters (Zydis® technology) is required. The ODT of the present invention may be prepared using a direct compression technique, comprising the method steps of:
i) preparing a powder mixture containing crystalline asenapine maleate and pharmaceutical excipients, and
ii) subjecting the powder mixture obtained in step (i) to compression to obtain the tablet.

Alternatively, the ODT may be prepared by dry granulation comprising the method steps of:
i) preparing a powder mixture containing crystalline asenapine maleate and at least one pharmaceutical excipient,
ii) compacting the powder mixture obtained in step (i) to form a comprimate,
iii) converting the comprimate obtained in step (ii) into a granulate,
iv) optionally mixing the granulate obtained in step (iii) with a pharmaceutical excipient, and
v) subjecting the granulate obtained in step (iii) or the mixture obtained in step (iv) to compression to obtain the tablet.

According to a preferred embodiment of the dry granulation procedure, the powder mixture in step (i) contains crystalline asenapine maleate and L-HPC. Preferably, the powder mixture in step (i) consists of crystalline asenapine maleate and L-HPC, and the granulate obtained in step (iii) is mixed with a pharmaceutical excipient.

Preferably, method step (ii) is carried out using roller compaction or slugging techniques, while method step (iii) is carried out by screening or milling the comprimate.

Alternatively, the ODT may be prepared by wet granulation comprising the method steps of:
i) preparing a powder mixture containing crystalline asenapine maleate and at least one pharmaceutical excipient,
ii) granulating the mixture obtained in step (i) with a granulation liquid to form a wet granulate,
iii) drying the wet granulate obtained in step (ii) to form a dry granulate,
iv) optionally mixing the granulate obtained in step (iii) with a pharmaceutical excipient, and
v) subjecting the granulate obtained in step (iii) or the mixture obtained in step (iv) to compression to obtain the tablet.

According to a preferred embodiment of the wet granulation procedure, the granulate obtained in step (iii) is mixed with a pharmaceutical excipient and a carboxylic acid. According to an even more preferred embodiment of the wet granulation procedure, the granulation liquid in step (ii) consists of isopropyl alcohol and it contains povidone.

In the third aspect of the invention, the ODT of the present invention is prepared using conventional tabletting techniques as direct compression and dry granulation. No lyophilization of a premix within blisters (Zydis® technology) is required. The ODT of the present invention may be prepared using a direct compression technique, comprising the method steps of:
i) preparing a mixture consisting of asenapine maleate, a carboxylic acid and pharmaceutical excipients, and
ii) subjecting the mixture obtained in step (i) to compression to obtain the tablet.

Alternatively, the ODT may be prepared by dry granulation comprising the method steps of:
i) preparing a mixture containing asenapine maleate, a pharmaceutical excipient and optionally a carboxylic acid,
ii) compacting the mixture obtained in step (i) to form a comprimate,
iii) converting the comprimate obtained in step (ii) into a granulate,
iv) mixing the granulate obtained in step (iii) with a pharmaceutical excipient and optionally a carboxylic acid, and
v) subjecting the mixture obtained in step (iv) to compression to obtain the tablet, wherein at least in one of method steps (i) and (iv) a carboxylic acid is used.

According to a preferred embodiment of the dry granulation procedure, the granulate obtained in step (iii) is mixed with a pharmaceutical excipient and a carboxylic acid. According to an even more preferred embodiment of the dry granulation procedure, the mixture in step (i) consists of asenapine maleate and L-HPC.

Alternatively, the ODT may be prepared by wet granulation comprising the method steps of:
i) preparing a mixture containing asenapine maleate, a pharmaceutical excipient and optionally a carboxylic acid,
ii) granulating the mixture obtained in step (i) with a granulation liquid to form a wet granulate,
iii) drying the wet granulate obtained in step (ii) to form a dry granulate,
iv) mixing the granulate obtained in step (iii) with a pharmaceutical excipient and optionally a carboxylic acid, and
v) subjecting the mixture obtained in step (iv) to compression to obtain the tablet, wherein at least in one of method steps (i) and (iv) a carboxylic acid is used.

According to a preferred embodiment of the wet granulation procedure, the granulate obtained in step (iii) is mixed with a pharmaceutical excipient and a carboxylic acid. According to an even more preferred embodiment of the wet granulation procedure, the granulation liquid in step (ii) consists of isopropyl alcohol and it contains povidone.

In all three aspects of the invention, suitable excipients, which may be used for preparing the ODT of the present invention, are selected from disintegrants, surfactants, glidants, lubricants, fillers, flavorants and sweeteners. Examples of disintegrants include sodium starch glycolate, crospovidone and croscarmellose sodium, as well as coprocessed excipients made from mannitol and maize starch (Pearlitol® Flash; Roquette), mannitol, polyvinylacetate and crospovidone (Ludiflash®; BASF) or F-melt® (Fuji Chemical Industry Co. Ltd.). Examples of surfactants include sodium laurylsulphate, poloxamers and polysorbates, e.g. polysorbate 80. Suitable glidants are silicon dioxide and talk, and suitable lubricants include magnesium stearate and sodium stearyl fumarate. Flavorants, such as black cherry flavour, and sweeteners, such as acesulfame potassium and aspartame may be employed. Furthermore additional suitable excipients, which may be used for preparing the ODT of the present invention, are binders. Examples of binders include methyl cellulose, hydroxypropylmethyl cellulose, hydroxypropyl cellulose, povidone, copovidone, and polyvinyl alcohol/polyethylene glycol graft copolymer (Kollicoat® IR; BASF).

According to a preferred embodiment of the first and second aspect of the present invention, the ODT contains a carboxylic acid, e.g. tartaric acid, as a pH-adjusting agent. If the ODT is prepared by dry granulation, the pharmaceutical excipients other than L-HPC are preferably present in the ODT only as extragranular components.

With regard to the third aspect of the invention, it was found that the presence of a carboxylic acid in an asenapine maleate containing ODT resulted in enhanced storage stability. Hence, the present invention relates to the use of a carboxylic acid as defined above as a pharmaceutical excipient for enhancing storage stability of an ODT containing asenapine maleate.

The invention is further illustrated by reference to the following examples.

EXAMPLES

The dissolution rates of asenapine maleate from the orally disintegrating tablet of the present invention and the comparative ODTs, including the Saphris® 5 mg & 10 mg tablets, have been determined in simulated salivary fluid (composition "SS 1" reported on page 21, Table 10, in the article "Simulated Biological Fluids with Possible Application in Dissolution Testing" by M. R. C. Marques et. al. in *Dissolution Technologies*, August 2011, 15-28, i.e.: 0.72 g/l potassium chloride, 0.22 g/l calcium chloride dihydrate, 0.6 g/l sodium chloride, 0.68 g/l potassium phosphate monobasic, 0.866 g/l sodium phosphate dibasic dodecahydrate, 1.5 g/l potassium bicarbonate, 0.06 g/l potassium thiocyanate, and 0.03 g/l citric acid) at 37±0.5° C. according to the dissolution test described in the European Pharmacopeia 7.0, 2.9.3 (500 ml; pH 6.5; 50 rpm). The dissolution rate is reported as the active ingredient release [%] over time [min].

Stability testing (40° C./75% RH) was conducted according to Guideline Q 1 A (R2) of International Conference on Harmonization (ICH).

The ODTs described in the examples and comparative examples contain the monoclinic form H of asenapine maleate in micronized form: D(10)=1.343 µm, D(50)=5.720 µm and D(90)=13.135 µm (Mastersizer 2000).

First Aspect of the Invention

Comparative Example 1

| Ingredients | [mg] |
|---|---|
| Stage-A (Dry mix and Compaction) | |
| Asenapine Maleate | 14.11 |
| Mannitol (Pearlitol ® 200 SD) | 11.65 |
| Sodium Starch Glycolate (Type A) | 1.00 |
| Maltodextrin (Glucidex ® 19 D) | 3.00 |
| Magnesium Stearate | 0.75 |
| Stage-B (Lubrication and Blending) | |
| Pearlitol Flash ® | 27.32 |
| Aspartame | 0.30 |
| Black Cherry Flavour | 0.12 |
| Tartaric Acid | 1.00 |
| Magnesium Stearate | 0.75 |
| Total weight | 60.00 |
| Physical parameters | |
| Resistance to crushing (Newton) | 14-18 |
| Disintegration Time (Sec) | 12 |

| Mean Cumulative % Labeled Amount Dissolved | | | | | | | | |
|---|---|---|---|---|---|---|---|---|
| | 1 min | 3 min | 5 min | 10 min | 15 min | 20 min | 30 min | 45 min | 60 min |
| Saphris ® 10 mg | 63 | 95 | 99 | 100 | 100 | 100 | 100 | 99 | 99 |
| Comparative Example 1 | 49 | 71 | 80 | 85 | 88 | 89 | 90 | 92 | 92 |

Procedure:

Asenapine maleate, mannitol, sodium starch glycolate, maltodextrin and magnesium stearate were sifted, blended and subsequently subjected to compaction. The resulting dry granules were mixed with Pearlitol Flash®, aspartame, black cherry flavour, tartaric acid and magnesium stearate, and compressed into tablets. A rapid dissolution of the drug is required for an ODT. Preferably, more than 90% of the drug should be released within three minutes. The use of sodium starch glycolate and Pearlitol Flash® as disintegrants did not provide a sufficiently high dissolution rate.

Comparative Example 2

| Ingredients | [mg] |
|---|---|
| Stage-A (Dry mix and Compaction) | |
| Asenapine Maleate | 14.11 |
| Mannitol (Pearlitol ® 200 SD) | 11.45 |
| Maltodextrin (Glucidex ® 19 D) | 3.00 |
| Croscarmellose Sodium | 1.20 |
| Magnesium Stearate | 0.75 |
| Stage-B (Lubrication and Blending) | |
| Pearlitol Flash ® | 27.32 |
| Aspartame | 0.30 |
| Black Cherry Flavour | 0.12 |
| Tartaric Acid | 1.00 |
| Magnesium Stearate | 0.75 |
| Total weight | 60.00 |
| Physical parameters | |
| Resistance to crushing (Newton) | 14-21 |
| Disintegration Time (Sec) | 14 |

| Mean Cumulative % Labeled Amount Dissolved | | | | | | | | |
|---|---|---|---|---|---|---|---|---|
| | 1 min | 3 min | 5 min | 10 min | 15 min | 20 min | 30 min | 45 min | 60 min |
| Saphris ® 10 mg | 63 | 95 | 99 | 100 | 100 | 100 | 100 | 99 | 99 |
| Comparative Example 2 | 30 | 52 | 63 | 74 | 76 | 77 | 80 | 82 | 85 |

Procedure:

The tablet was produced as indicated in comparative example 1, except that croscarmellose sodium was used instead of sodium starch glycolate as intragranular disintegrant. The use of croscarmellose sodium did not improve the dissolution rate of the drug.

Comparative Example 3

| Ingredients | [mg] |
|---|---|
| Stage-A (Dry mix and Compaction) | |
| Asenapine Maleate | 14.21 |
| Mannitol (Pearlitol ® 200 SD) | 10.00 |
| Sodium Starch Glycolate (Type A) | 1.00 |
| Maltodextrin (Glucidex ® 19 D) | 3.00 |
| Poloxamer (Lutrol ® Micro 127) | 2.00 |
| Stage-B (Lubrication and Blending) | |
| Pearlitol Flash ® | 28.04 |
| Tartaric Acid | 1.00 |
| Sodium Starch Glycolate (Type A) | 2.00 |
| Magnesium Stearate | 0.75 |
| Total weight | 62.00 |
| Physical parameters | |
| Resistance to crushing (Newton) | 15-22 |
| Disintegration Time (Sec) | 20 sec |

| Mean Cumulative % Labeled Amount Dissolved | | | | | | | | |
|---|---|---|---|---|---|---|---|---|
| | 1 min | 3 min | 5 min | 10 min | 15 min | 20 min | 30 min | 45 min | 60 min |
| Saphris ® 10 mg | 63 | 95 | 99 | 100 | 100 | 100 | 100 | 99 | 99 |
| Comparative Example 3 | 28 | 54 | 67 | 77 | 83 | 86 | 89 | 92 | 93 |

Procedure:

The tablet was produced as indicated in comparative example 1, except that poloxamer was additionally contained as intragranular component. The addition of the surfactant poloxamer did not enhance the dissolution rate of the drug.

Comparative Examples 4 And 5

| Ingredients | Comparative Ex. 4 [mg] | Comparative Ex. 5 [mg] |
|---|---|---|
| Stage-A (Dry Mix) | | |
| Asenapine Maleate | 7.12 | 2.84 |
| Croscarmellose Sodium (Ac-Di-Sol ®) | 12.50 | 5.00 |
| Maize Starch | 12.50 | 5.00 |
| Acesulfame Potassium | 20.00 | 8.00 |
| Magnesium Stearate | 0.50 | 0.20 |
| Total weight | 52.62 | 21.04 |
| Physical parameters | | |
| Hardness (Newton) | 9-12 | 8-11 |
| Disintegration Time | 1 min 14 sec | 30 sec |

| [min] | Saphris ® 5 mg [%] | Comparative Ex. 4 [%] | Comparative Ex. 5 [%] |
|---|---|---|---|
| 1 | 48 | 15 | 21 |
| 3 | 85 | 38 | 37 |
| 5 | 94 | 47 | 43 |
| 10 | 97 | 53 | 48 |
| 15 | 97 | 56 | 51 |
| 20 | 97 | 61 | 57 |
| 30 | 97 | 74 | 71 |
| 45 | 97 | 85 | 78 |
| 60 | 97 | 90 | 81 |

Procedure:

The tablets described in comparative examples 4 and 5 have been prepared by direct compression as described in paragraph [0089] of WO 2008/040816. Instead of using amorphous asenapine maleate prepared by freeze-drying as described in WO 2008/040816, the crystalline monoclinic form H of asenapine maleate has been used in the comparative examples.

The use of the crystalline drug instead of its amorphous form led to lower dissolution rates. Hence, the formulation described in WO 2008/040816 is not suitable for a crystalline asenapine maleate in order to obtain an ODT.

Example 1

| Ingredients | [mg] |
|---|---|
| Stage-A (Dry mix and Compaction) | |
| Asenapine Maleate | 14.21 |
| Low Substituted Hydroxypropylcellulose (L-HPC LH-31) | 15.00 |
| Stage-B (Lubrication and Blending) | |
| Pearlitol Flash ® | 27.87 |
| Tartaric Acid | 0.75 |
| Magnesium Stearate | 1.75 |
| Aspartame | 0.30 |
| Black Cherry Flavour | 0.12 |
| Total weight | 60.00 |
| Physical parameters | |
| Resistance to crushing (Newton) | 14-20 |
| Disintegration Time (Sec) | 14 |

| Mean Cumulative % Labeled Amount Dissolved | | | | | | | | |
|---|---|---|---|---|---|---|---|---|
| | 1 min | 3 min | 5 min | 10 min | 15 min | 20 min | 30 min | 45 min | 60 min |
| Saphris® 10 mg | 63 | 95 | 99 | 100 | 100 | 100 | 100 | 99 | 99 |
| Example 1 | 71 | 92 | 96 | 99 | 100 | 100 | 101 | 101 | 101 |

Procedure:

The tablet was prepared as indicated in comparative example 1. The use of L-HPC as intragranular disintegrant results in an ODT with a sufficiently high dissolution rate of the drug.

Example 2

| Ingredients | [mg] |
|---|---|
| Stage-A (Dry mix and Compaction) | |
| Asenapine Maleate | 14.21 |
| Low Substituted Hydroxypropylcellulose (L-HPC LH-31) | 15.00 |
| Pearlitol Flash® | 27.87 |
| Tartaric Acid | 0.75 |
| Magnesium Stearate | 1.75 |
| Aspartame | 0.30 |
| Black Cherry Flavour | 0.12 |
| Total weight | 60.00 |
| Physical parameters | |
| Resistance to crushing (Newton) | 14-20 |
| Disintegration Time (Sec) | 40 |

| Mean Cumulative % Labeled Amount Dissolved | | | | | | | | |
|---|---|---|---|---|---|---|---|---|
| | 1 min | 3 min | 5 min | 10 min | 15 min | 20 min | 30 min | 45 min | 60 min |
| Saphris® 10 mg | 63 | 95 | 99 | 100 | 100 | 100 | 100 | 99 | 99 |
| Example 2 | 34 | 66 | 78 | 91 | 96 | 97 | 97 | 98 | 97 |

Procedure:

The composition of the tablet corresponds to the composition of the tablet described in example 1. The tablet was prepared by subjecting a mixture of asenapine maleate, L-HPC, Pearlitol Flash®, tartaric acid, magnesium stearate, aspartame and black cherry flavour to compression. Although direct compression was used, the use of L-HPC still results in an ODT with a relatively high dissolution rate of the drug (for a comparison, see the tablets described in comparative examples 4 and 5).

Examples 3-5 And Comparative Example 6

| Ingredients | Ex. 3 [mg] | Ex. 4 [mg] | Ex. 5 [mg] | Comp. Ex. 6 [mg] |
|---|---|---|---|---|
| Stage-A (Blend for compaction) | | | | |
| Asenapine Maleate | 14.06 | 14.06 | 14.06 | 14.06 |
| Low Substituted Hydroxypropylcellulose (L-HPC LH-31) | 15.00 | 15.00 | 15.00 | — |
| Croscarmellose Sodium (Ac-Di-Sol®) | — | — | — | 15.00 |
| Stage-B: (Blend for compression) | | | | |
| Pearlitol Flash® | 28.44 | — | — | 28.44 |
| F-Melt® (Type C) | — | 28.44 | — | — |
| Mannitol (Pearlitol® SD 200) | — | — | 28.44 | — |
| Tartaric acid | 0.75 | 0.75 | 0.75 | 0.75 |
| Magnesium Stearate | 1.75 | 1.75 | 1.75 | 1.75 |
| Total weight | 60.00 | 60.00 | 60.00 | 60.00 |
| Physical parameters | | | | |
| Resistance to crushing (Newton) | 11-17 | 13-23 | 11-22 | 12-21 |
| Disintegration Time (Sec) | 15 | 35 | 18 | 17 |

| [min] | Saphris® 10 mg [%] | Example 3 [%] | Example 4 [%] | Example 5 [%] | Comparative Ex. 6 [%] |
|---|---|---|---|---|---|
| 1 | 63 | 64 | 56 | 61 | 41 |
| 3 | 95 | 87 | 87 | 83 | 79 |
| 5 | 99 | 92 | 91 | 86 | 87 |
| 10 | 100 | 96 | 93 | 90 | 90 |
| 15 | 100 | 97 | 95 | 91 | 91 |
| 20 | 100 | 98 | 95 | 93 | 91 |
| 30 | 100 | 97 | 94 | 93 | 91 |
| 45 | 99 | 98 | 96 | 94 | 91 |
| 60 | 99 | 98 | 95 | 94 | 91 |

Procedure:

The tablets were produced as indicated in comparative example 1. In comparative example 6, an unusually high amount of the disintegrant croscarmellose sodium was used. Replacing L-HPC with the same amount of a stronger disintegrant as croscarmellose sodium does not affect the disintegration time, but provides a tablet with a lower dissolution rate of the drug.

Second Aspect of the Invention

Example 6

| Ingredients | [mg] |
| --- | --- |
| Stage-A (Dry mix and Compaction) | |
| Asenapine Maleate | 14.11 |
| Mannitol (Pearlitol ® 200 SD) | 11.65 |
| Sodium Starch Glycolate (Type A) | 1.00 |
| Maltodextrin (Glucidex ® 19 D) | 3.00 |
| Magnesium Stearate | 0.75 |
| Stage-B (Lubrication and Blending) | |
| Pearlitol Flash ® | 27.32 |
| Aspartame | 0.30 |
| Black Cherry Flavour | 0.12 |
| Tartaric Acid | 1.00 |
| Magnesium Stearate | 0.75 |
| Total weight | 60.00 |
| Physical parameters | |
| Resistance to crushing (Newton) | 14-18 |
| Disintegration Time (Sec) | 12 |

Procedure:

Asenapine maleate, mannitol, sodium starch glycolate, maltodextrin and magnesium stearate were sifted, blended and subsequently subjected to compaction. The resulting dry granules were mixed with Pearlitol Flash®, aspartame, black cherry flavour, tartaric acid and magnesium stearate, and compressed into tablets.

Example 7

| Ingredients | [mg] |
| --- | --- |
| Stage-A (Dry mix and Compaction) | |
| Asenapine Maleate | 14.11 |
| Mannitol (Pearlitol ® 200 SD) | 11.45 |
| Maltodextrin (Glucidex ® 19 D) | 3.00 |
| Croscarmellose Sodium | 1.20 |
| Magnesium Stearate | 0.75 |
| Stage-B (Lubrication and Blending) | |
| Pearlitol Flash ® | 27.32 |
| Aspartame | 0.30 |
| Black Cherry Flavour | 0.12 |
| Tartaric Acid | 1.00 |
| Magnesium Stearate | 0.75 |
| Total weight | 60.00 |
| Physical parameters | |
| Resistance to crushing (Newton) | 14-21 |
| Disintegration Time (Sec) | 14 |

Procedure:

The tablet was produced as indicated in example 6, except that croscarmellose sodium was used instead of sodium starch glycolate as intragranular disintegrant.

Example 8

| Ingredients | [mg] |
| --- | --- |
| Stage-A (Dry mix and Compaction) | |
| Asenapine Maleate | 14.21 |
| Mannitol (Pearlitol ® 200 SD) | 10.00 |
| Sodium Starch Glycolate (Type A) | 1.00 |
| Maltodextrin (Glucidex ® 19 D) | 3.00 |
| Poloxamer (Lutrol ® Micro 127) | 2.00 |
| Stage-B (Lubrication and Blending) | |
| Pearlitol Flash ® | 28.04 |
| Tartaric Acid | 1.00 |
| Sodium Starch Glycolate (Type A) | 2.00 |
| Magnesium Stearate | 0.75 |
| Total weight | 62.00 |
| Physical parameters | |
| Resistance to crushing (Newton) | 15-22 |
| Disintegration Time (Sec) | 20 sec |

Procedure:

The tablet was produced as indicated in example 6, except that poloxamer was additionally contained as intragranular component.

Example 9

| Ingredients | [mg] |
| --- | --- |
| Stage-A (Dry mix and Compaction) | |
| Asenapine Maleate | 14.21 |
| Low Substituted Hydroxypropylcellulose (L-HPC LH-31) | 15.00 |
| Stage-B (Lubrication and Blending) | |
| Pearlitol Flash ® | 27.87 |
| Tartaric Acid | 0.75 |
| Magnesium Stearate | 1.75 |
| Aspartame | 0.30 |
| Black Cherry Flavour | 0.12 |
| Total weight | 60.00 |
| Physical parameters | |
| Resistance to crushing (Newton) | 14-20 |
| Disintegration Time (Sec) | 14 |

Procedure:

The tablet was prepared as indicated in example 6.

Example 10

| Ingredients | [mg] |
| --- | --- |
| Stage-A (Dry mix and Compaction) | |
| Asenapine Maleate | 14.21 |
| Low Substituted Hydroxypropylcellulose (L-HPC LH-31) | 15.00 |
| Pearlitol Flash ® | 27.87 |
| Tartaric Acid | 0.75 |
| Magnesium Stearate | 1.75 |
| Aspartame | 0.30 |
| Black Cherry Flavour | 0.12 |
| Total weight | 60.00 |

-continued

| Ingredients | [mg] |
|---|---|
| Physical parameters | |
| Resistance to crushing (Newton) | 14-20 |
| Disintegration Time (Sec) | 40 |

Procedure:

The composition of the tablet corresponds to the composition of the tablet described in example 9. The tablet was prepared by subjecting a mixture of asenapine maleate, L-HPC, Pearlitol Flash®, tartaric acid, magnesium stearate, aspartame and black cherry flavour to compression, i.e. by direct compression.

Examples 11-14

| Ingredients | Ex. 11 [mg] | Ex. 12 [mg] | Ex. 13 [mg] | Ex. 14 [mg] |
|---|---|---|---|---|
| Stage-A (Blend for compaction) | | | | |
| Asenapine Maleate | 14.06 | 14.06 | 14.06 | 14.06 |
| Low Substituted Hydroxypropylcellulose (L-HPC LH-31) | 15.00 | 15.00 | 15.00 | — |
| Croscarmellose Sodium (Ac-Di-Sol ®) | — | — | — | 15.00 |
| Stage-B: (Blend for compression) | | | | |
| Pearlitol Flash ® | 28.44 | — | — | 28.44 |
| F-Melt ® (Type C) | — | 28.44 | — | — |
| Mannitol (Pearlitol ® SD 200) | — | — | 28.44 | — |
| Tartaric acid | 0.75 | 0.75 | 0.75 | 0.75 |
| Magnesium Stearate | 1.75 | 1.75 | 1.75 | 1.75 |
| Total weight | 60.00 | 60.00 | 60.00 | 60.00 |
| Physical parameters | | | | |
| Resistance to crushing (Newton) | 11-17 | 13-23 | 11-22 | 12-21 |
| Disintegration Time (Sec) | 15 | 35 | 18 | 17 |

Procedure:

The tablets were produced as indicated in example 6.

Third Aspect of the Invention

Example 15

| Ingredients | [mg] |
|---|---|
| Stage-A (Dry mix and Compaction) | |
| Asenapine Maleate | 14.11 |
| Mannitol (Pearlitol ® 200 SD) | 11.65 |
| Sodium Starch Glycolate (Type A) | 1.00 |
| Maltodextrin (Glucidex ® 19 D) | 3.00 |
| Magnesium Stearate | 0.75 |
| Stage-B (Lubrication and Blending) | |
| Pearlitol Flash ® | 27.32 |
| Aspartame | 0.30 |
| Black Cherry Flavour | 0.12 |
| Tartaric Acid | 1.00 |
| Magnesium Stearate | 0.75 |
| Total weight | 60.00 |

Procedure:

Asenapine maleate, mannitol, sodium starch glycolate, maltodextrin and magnesium stearate were sifted, blended and subsequently subjected to compaction. The resulting dry granules were mixed with Pearlitol Flash®, aspartame, black cherry flavour, tartaric acid and magnesium stearate, and compressed into tablets.

Comparative Example 7

| Ingredients | [mg] |
|---|---|
| Stage-A (Dry mix and Compaction) | |
| Asenapine Maleate | 14.11 |
| Mannitol (Pearlitol ® 200 SD) | 11.65 |
| Sodium Starch Glycolate (Type A) | 1.00 |
| Maltodextrin (Glucidex ® 19 D) | 3.00 |
| Magnesium Stearate | 0.75 |
| Stage-B (Lubrication and Blending) | |
| Pearlitol Flash ® | 28.32 |
| Aspartame | 0.30 |
| Black Cherry Flavour | 0.12 |
| Magnesium Stearate | 0.75 |
| Total weight | 60.00 |

Procedure:

The tablet was produced as indicated in example 15, except that tartaric acid was not used.

Examples 16-18

| Ingredients | Ex. 16 [mg] | Ex. 17 [mg] | Ex. 18 [mg] |
|---|---|---|---|
| Stage-A (Dry mix and Compaction) | | | |
| Asenapine Maleate | 14.06 | 14.06 | 14.06 |
| Low Substituted Hydroxypropylcellulose (L-HPC LH-31) | 15.00 | 15.00 | 15.00 |
| Stage-B (Lubrication and Blending) | | | |
| Pearlitol Flash ® | 28.44 | 28.44 | 28.44 |
| Tartaric acid | 0.75 | — | — |
| Succinic acid | — | 0.75 | — |
| Fumaric acid | — | — | 0.75 |
| Magnesium Stearate | 1.75 | 1.75 | 1.75 |
| Total weight | 60.00 | 60.00 | 60.00 |

Procedure:

Asenapine maleate and low substituted hydroxypropylcellulose were sifted, blended and subsequently subjected to compaction. The resulting dry granules were mixed with Pearlitol Flash®, tartaric acid or alternatively succinic acid or fumaric acid, and magnesium stearate, and compressed into tablets.

Comparative Example 8

| Ingredients | [mg] |
|---|---|
| Stage-A (Dry mix and Compaction) | |
| Asenapine Maleate | 14.06 |
| Low Substituted Hydroxypropylcellulose | 15.00 |

| Ingredients | [mg] |
|---|---|
| (L-HPC LH-31) | |
| Stage-B (Lubrication and Blending) | |
| Pearlitol Flash ® | 29.19 |
| Magnesium Stearate | 1.75 |
| Total weight | 60.00 |

Procedure:

The tablet was produced as indicated in example 16, except that tartaric acid was not used.

First, Second, and Third Aspects of the Invention

Example 19

| Ingredients | [mg] |
|---|---|
| Stage-A (Dry mix and Compaction) | |
| Asenapine Maleate | 14.08 |
| Low Substituted Hydroxypropylcellulose (L-HPC LH-31) | 10.00 |
| Citric Acid Anhydrous | 1.90 |
| Stage-B (Lubrication and Blending) | |
| Mannitol (Pearlitol ® SD 200) | 29.27 |
| Crospovidone (Polyplasdone XL-10) | 2.00 |
| Sodium Hydrogen Carbonate | 1.00 |
| Magnesium Stearate | 1.75 |
| Total weight | 60.00 |
| Physical parameters | |
| Resistance to crushing (Newton) | 13-19 |
| Disintegration Time (Sec) | 15 |

Procedure:

Asenapine maleate, low-substituted hydroxypropylcellulose, and citric acid were sifted, blended and subsequently subjected to compaction. The resulting dry granules were mixed with mannitol, crospovidone, sodium hydrogen carbonate, and magnesium stearate, and compressed into tablets. The use of L-HPC as intragranular disintegrant results in an ODT with a sufficiently high dissolution rate of the drug.

Examples 20-23

| Ingredients | Ex. 20 [mg] | Ex. 21 [mg] | Ex. 22 [mg] | Ex. 23 [mg] |
|---|---|---|---|---|
| Stage-A (Dry mix) | | | | |
| Asenapine Maleate | 14.08 | 14.06 | 14.06 | 14.08 |
| Low Substituted Hydroxypropylcellulose (L-HPC LH-21) | 5.00 | 5.00 | 5.00 | 5.00 |
| Microcrystalline Cellulose (Comprecel 101D+) | 31.02 | 33.44 | 33.44 | 31.02 |
| Crospovidone (Polyplasdone XL-10) | 3.00 | 3.00 | 3.00 | 3.00 |
| Stage-B (Binder Solution) | | | | |
| Povidone | 1.50 | 1.50 | 1.50 | 1.50 |
| Isopropyl Alcohol | q.s. | q.s. | q.s. | q.s. |
| Stage-C (Blending and Lubrication) | | | | |
| Tartaric Acid | 1.60 | — | 1.60 | — |
| Citric Acid Anhydrous | — | — | — | 1.60 |
| Crospovidone (Polyplasdone XL-10) | 2.00 | 2.00 | 2.00 | 2.00 |
| Sodium Hydrogen Carbonate | 0.8 | — | — | — |
| Sodium Bicarbonate | — | — | 0.80 | 0.80 |
| Magnesium Stearate | 1.00 | 1.00 | 1.00 | 1.00 |
| Total weight | 60.00 | 60.00 | 62.40 | 60.00 |
| Physical parameters | | | | |
| Resistance to crushing (Newton) | 14-19 | 16-20 | 11-15 | 13-22 |
| Disintegration Time (Sec) | 10 | 13 | 15 | 10-15 |

| | Mean Cumulative % Labeled Amount Dissolved | | | | |
|---|---|---|---|---|---|
| | 1 min | 3 min | 5 min | 10 min | 15 min |
| Saphris ® 10 mg | 63 | 95 | 99 | 100 | 100 |
| Example 20 | 83 | 91 | 94 | 98 | 98 |
| Example 23 | 81 | 88 | 91 | 95 | 96 |

Procedure:

Asenapine maleate, low-substituted hydroxypropylcellulose, microcrystalline cellulose, and crospovidone were sifted and blended, and subsequently wet granulated with a binder solution of povidone dissolved in isopropyl alcohol. The resulting wet granules were dried and sifted, and subsequently mixed with crospovidone and magnesium stearate, and compressed into tablets (ex. 21), or further mixed with tartaric acid and sodium hydrogen carbonate (ex. 20), tartaric acid and sodium bicarbonate (ex. 22), or citric acid and sodium bicarbonate (ex. 23), followed by compression.

The use of L-HPC as intragranular disintegrant results in an ODT with a sufficiently high dissolution rate of the drug Example 24

| Ingredients | [mg] |
|---|---|
| Stage-A (Dry mix and Compaction) | |
| Asenapine Maleate | 14.08 |
| Low Substituted Hydroxypropylcellulose (L-HPC LH-31) | 15.00 |
| Stage-B (Lubrication and Blending) | |
| Pearlitol Flash ® | 28.42 |
| Maleic acid | 0.75 |
| Magnesium Stearate | 1.75 |
| Total weight | 60.00 |

Procedure:

The tablet was produced as indicated in example 16, except that maleic acid was used instead of tartaric acid.

Example 25

TABLE

Stability test (40° C./75% relative humidity)

Total impurities [%]

| | Initial | 1 month | 2 months | 3 months | 6 months |
|---|---|---|---|---|---|
| Example 15 | 0.10 | 0.06 | 0.08 | 0.08 | — |
| Comparative Example 7 | 0.23 | 0.23 | 0.35 | 0.30 | — |
| Example 16 | 0.11 | 0.13 | 0.19 | 0.21 | 0.21 |
| Comparative Example 8 | 0.16 | 0.26 | 0.28 | 0.26 | 0.43 |
| Example 17 | 0.18 | 0.16 | 0.19 | 0.21 | 0.18 |
| Example 18 | 0.17 | 0.16 | 0.18 | 0.22 | 0.18 |
| Example 24 | 0.17 | 0.17 | 0.27 | 0.20 | 0.19 |

Embodiments of the First Aspect of the Invention

1. Orally disintegrating tablet containing asenapine maleate, low substituted hydroxypropylcellulose (L-HPC), and a pharmaceutical excipient.

2. Orally disintegrating tablet according to embodiment 1, wherein the tablet is prepared by dry granulation.

3. Orally disintegrating tablet according to embodiment 2, wherein the tablet contains asenapine maleate and L HPC as intragranular components.

4. Orally disintegrating tablet according to embodiment 3, wherein the tablet contains asenapine maleate and L HPC as the sole intragranular components.

5. Orally disintegrating tablet according to any one of the preceding embodiments, wherein the weight ratio of asenapine maleate to L-HPC is from 0.5 to 1.5, preferably 0.7 to 1.2, and more preferred 0.9 to 1.1.

6. Orally disintegrating tablet according to any one of the preceding embodiments containing crystalline asenapine maleate, preferably monoclinic asenapine maleate (form H).

7. Process for preparing an orally disintegrating tablet according to embodiment 1 comprising the method steps of:
   i) preparing a mixture consisting of asenapine maleate, L-HPC and pharmaceutical excipients, and
   ii) subjecting the mixture obtained in step (i) to compression to obtain the tablet.

8. Process for preparing an orally disintegrating tablet according to embodiment 1 comprising the method steps of:
   i) preparing a mixture containing asenapine maleate and L-HPC,
   ii) compacting the mixture obtained in step (i) to form a comprimate,
   iii) converting the comprimate obtained in step (ii) into a granulate,
   iv) optionally mixing the granulate obtained in step (iii) with a pharmaceutical excipient, and
   v) subjecting the granulate obtained in step (iii) or the mixture obtained in step (iv) to compression to obtain the tablet.

9. Process according to embodiment 8, wherein the mixture in step (i) consists of asenapine maleate and L-HPC, and wherein the granulate obtained in step (iii) is mixed with a pharmaceutical excipient.

10. Process according to embodiment 8 or 9, wherein method step (ii) is carried out using roller compaction or slugging techniques.

11. Process according to any one of embodiments 8 to 10, wherein method step (iii) is carried out by screening or milling the comprimate.

12. Process according to any one of embodiments 7 to 11, wherein the orally disintegrating tablet contains crystalline asenapine maleate, preferably monoclinic asenapine maleate (form H).

Embodiments of the Second Aspect of the Invention

13. Orally disintegrating tablet containing asenapine maleate in crystalline form, wherein the tablet is prepared by compressing a mixture containing crystalline asenapine maleate and pharmaceutical excipients.

14. Orally disintegrating tablet according to embodiment 13, wherein the asenapine maleate is monoclinic asenapine maleate (form H), orthorhombic asenapine maleate (form L) or a mixture of the forms H and L.

15. Orally disintegrating tablet according to embodiment 13 or 14, wherein the tablet contains low substituted hydroxypropylcellulose (L HPC) as pharmaceutical excipient.

16. Orally disintegrating tablet according to any one of the embodiments 13 to 15, wherein the mixture is obtained by granulation, preferably dry granulation.

17. Orally disintegrating tablet according to embodiment 16, wherein the tablet contains asenapine maleate and L HPC as intragranular components.

18. Orally disintegrating tablet according to embodiment 17, wherein the tablet contains asenapine maleate and L HPC as the sole intragranular components.

19. Orally disintegrating tablet according to any one of embodiments 15 to 18, wherein the weight ratio of asenapine maleate to L-HPC is from 0.5 to 1.5, preferably 0.7 to 1.2, and more preferred 0.9 to 1.1.

20. Process for preparing an orally disintegrating tablet according to embodiment 13 comprising the method steps of:
   i) preparing a powder mixture containing crystalline asenapine maleate and pharmaceutical excipients, and
   ii) subjecting the powder mixture obtained in step (i) to compression to obtain the tablet.

21. Process for preparing an orally disintegrating tablet according to embodiment 13 comprising the method steps of:
   i) preparing a powder mixture containing crystalline asenapine maleate and at least one pharmaceutical excipient,
   ii) compacting the powder mixture obtained in step (i) to form a comprimate,
   iii) converting the comprimate obtained in step (ii) into a granulate,
   iv) optionally mixing the granulate obtained in step (iii) with a pharmaceutical excipient, and
   v) subjecting the granulate obtained in step (iii) or the mixture obtained in step (iv) to compression to obtain the tablet.

22. Process according to embodiment 21, wherein the powder mixture in step (i) contains crystalline asenapine maleate and L-HPC.

23. Process according to embodiment 22, wherein the powder mixture in step (i) consists of crystalline asenapine maleate and L-HPC, and wherein the granulate obtained in step (iii) is mixed with a pharmaceutical excipient.

Embodiments of the Third Aspect of the Invention

24. Orally disintegrating tablet containing asenapine maleate, a carboxylic acid and a pharmaceutical excipient.

25. Orally disintegrating tablet according to embodiment 24, wherein the carboxylic acid is selected from monocarboxylic acid, dicarboxylic acid, tricarboxylic acid, and mixtures thereof.

26. Orally disintegrating tablet according to embodiment 24 or 25, wherein the carboxylic acid is a $C_{2-6}$ carboxylic acid optionally substituted with at least one of hydroxy, amino and mercapto.

27. Orally disintegrating tablet according to embodiment 26, wherein the carboxylic acid is selected from glycolic acid, oxalic acid, malonic acid, succinic acid, maleic acid, fumaric acid, tartaric acid, malic acid, glutaric acid, citric acid and gluconic acid.

28. Orally disintegrating tablet according to embodiment 26, wherein the carboxylic acid is a $C_4$ dicarboxylic acid optionally substituted with hydroxy, preferably tartaric acid.

29. Orally disintegrating tablet according to any one of the embodiments 24 to 28, wherein the carboxylic acid is contained in the tablet in an amount of 0.2 to 2.0% by weight, preferably 0.5 to 1.5% by weight and more preferred 0.75 to 1.25% by weight, based on the total weight of the tablet.

30. Orally disintegrating tablet according to any one of the embodiments 24 to 29, wherein the tablet contains low substituted hydroxypropylcellulose (L-HPC) as pharmaceutical excipient.

31. Orally disintegrating tablet according to any one of the embodiments 24 to 30, wherein the tablet is obtained by granulation, preferably dry granulation.

32. Orally disintegrating tablet according to embodiment 31, wherein the tablet contains asenapine maleate and L-HPC as intragranular components.

33. Orally disintegrating tablet according to embodiment 32, wherein the tablet contains asenapine maleate and L-HPC as the sole intragranular components.

34. Orally disintegrating tablet according to embodiment 32 or 33, wherein the weight ratio of asenapine maleate to L-HPC is from 0.5 to 1.5, preferably 0.7 to 1.2, and more preferred 0.9 to 1.1.

35. Orally disintegrating tablet according to according to any one of embodiments 31 to 34, wherein the tablet contains the carboxylic acid as extragranular component.

36. Orally disintegrating tablet according to any one of the embodiments 24 to 35 containing crystalline asenapine maleate, preferably monoclinic asenapine maleate.

37. Process for preparing an orally disintegrating tablet according to embodiment 24 comprising the method steps of:
   i) preparing a mixture consisting of asenapine maleate, a carboxylic acid and pharmaceutical excipients, and
   ii) subjecting the mixture obtained in step (i) to compression to obtain the tablet.

38. Process for preparing an orally disintegrating tablet according to embodiment 24 comprising the method steps of:
   i) preparing a mixture containing asenapine maleate, a pharmaceutical excipient and optionally a carboxylic acid,
   ii) compacting the mixture obtained in step (i) to form a comprimate,
   iii) converting the comprimate obtained in step (ii) into a granulate,
   iv) mixing the granulate obtained in step (iii) with a pharmaceutical excipient and optionally a carboxylic acid, and
   v) subjecting the mixture obtained in step (iv) to compression to obtain the tablet,
   wherein at least in one of method steps (i) and (iv) a carboxylic acid is used.

39. Process according to embodiment 38, wherein the granulate obtained in step (iii) is mixed with a pharmaceutical excipient and a carboxylic acid.

40. Process according to embodiment 39, wherein the mixture in step (i) consists of asenapine maleate and L-HPC.

41. Use of a carboxylic acid as a pharmaceutical excipient for enhancing storage stability of an orally disintegrating tablet containing asenapine maleate.

42. Use according to embodiment 41, wherein the carboxylic acid is an acid as defined in embodiments 25 to 28.

The invention claimed is:

1. An orally disintegrating tablet comprising asenapine maleate, a carboxylic acid in an amount of 0.2 to 2.0% by weight based on total weight of the tablet, and one or more pharmaceutical excipients, wherein said tablet is stable at 40° C. and 75% rH for at least 3 months compared to a tablet having no carboxylic acid.

2. The orally disintegrating tablet according to claim 1, wherein the tablet is prepared by dry granulation.

3. The orally disintegrating tablet according to claim 1, wherein the tablet is prepared by wet granulation.

4. The orally disintegrating tablet according to claim 1, wherein said carboxylic acid is a branched or unbranched, saturated or unsaturated carboxylic acid containing 2 to 10 carbon atoms optionally substituted with one or more hydroxy (—OH), amino (—NH2) and/or mercapto (—SH) groups.

5. The orally disintegrating tablet according to claim 1, wherein the carboxylic acid is selected from monocarboxylic acid, dicarboxylic acid, tricarboxylic acid, and mixtures thereof.

6. The orally disintegrating tablet according to claim 1, wherein the carboxylic acid is selected from glycolic acid, oxalic acid, malonic acid, succinic acid, maleic acid, fumaric acid, tartaric acid, malic acid, glutaric acid, citric acid and gluconic acid.

7. The orally disintegrating tablet according to claim 1, wherein the carboxylic acid is a $C_4$ dicarboxylic acid optionally substituted with hydroxy.

8. The orally disintegrating tablet according to claim 1, wherein the carboxylic acid is contained in the tablet in an amount of 0.5 to 1.5% by weight, based on the total weight of the tablet.

9. The orally disintegrating tablet according to claim 7, wherein the $C_4$ dicarboxylic acid is tartaric acid.

10. The orally disintegrating tablet according to claim 1, wherein said excipients comprise one or more disintegrants, surfactants, glidants, lubricants, fillers, flavorants and sweeteners.

11. The orally disintegrating tablet according to claim 1, containing crystalline asenapine maleate.

12. The orally disintegrating tablet according to claim 11, wherein said crystalline asenapine maleate is monoclinic asenapine maleate (form H).

13. The orally disintegrating tablet according to claim 1, wherein said asenapine maleate is in a micronized form and has a particle size distribution in which D(90) is equal or less than 90 µm, D(50) is equal or less than 20 µm and D(10) is equal or less than 10 µm.

14. The orally disintegrating tablet according to claim 8 wherein the carboxylic acid is contained in the tablet in an amount of 0.5 to 1.5% by weight based on the total weight of the tablet.

15. The orally disintegrating tablet according to claim 8 wherein the carboxylic acid is contained in the tablet in an amount of 0.75 to 1.25% by weight, based on the total weight of the tablet.

16. An orally disintegrating tablet comprising asenapine maleate, a carboxylic acid in an amount of 0.75 to 2.5% by weight based on total weight of the tablet, and one or more pharmaceutical excipients, wherein said tablet is stable at 40° C. and 75% rH for at least 3 months compared to a tablet having no carboxylic acid.

\* \* \* \* \*